United States Patent
Hart et al.

(10) Patent No.: US 7,338,466 B2
(45) Date of Patent: Mar. 4, 2008

(54) DRAINAGE CATHETER HAVING AN EXPANDABLE RETENTION MEMBER

(75) Inventors: Charles C. Hart, Summerville, SC (US); Raffi S. Pinedjian, Fountain Valley, CA (US); Boun Pravong, Corona, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 395 days.

(21) Appl. No.: 10/521,368

(22) PCT Filed: Jul. 11, 2003

(86) PCT No.: PCT/US03/21756

§ 371 (c)(1),
(2), (4) Date: Jan. 12, 2005

(87) PCT Pub. No.: WO2004/006984

PCT Pub. Date: Jan. 22, 2004

(65) Prior Publication Data

US 2005/0177102 A1   Aug. 11, 2005

(51) Int. Cl.
*A61M 31/00* (2006.01)
*A61M 37/00* (2006.01)

(52) U.S. Cl. ............................ 604/93.01; 604/95.04; 604/95.05

(58) Field of Classification Search ............ 604/95.03, 604/95.04, 96.01, 97.01, 97.02, 97.03, 98.01, 604/98.02, 99.01, 99.02, 99.03, 99.04, 100.01, 604/100.02, 101.03, 101.04, 101.05, 102.02, 604/102.03, 103, 103.01, 103.02, 103.03, 604/103.04, 103.05, 103.06, 103.07, 103.08, 604/103.09, 103.1, 103.11, 103.12, 103.13, 604/103.14, 914–921

See application file for complete search history.

(56) References Cited

U.S. PATENT DOCUMENTS

| 3,769,983 | A |   | 11/1973 | Merav |
| 4,148,319 | A | * | 4/1979 | Kasper et al. ......... 604/102.02 |
| 4,405,314 | A |   | 9/1983 | Cope |
| 4,407,271 | A |   | 10/1983 | Schiff |

(Continued)

FOREIGN PATENT DOCUMENTS

CA    2 414 225 A1 * 12/2001

*Primary Examiner*—Tatyana Zalukaeva
*Assistant Examiner*—Michael G Bogart
(74) *Attorney, Agent, or Firm*—Cynthia A. Bonner; Kenneth K. Vu; Richard L. Myers

(57) ABSTRACT

A drainage catheter is adapted to drain fluid from the body cavity through a body conduit and includes an elongate tube and a retention member disposed at the distal end of the elongate tube. The retention member is adapted for movement between a low-profile state facilitating insertion of the catheter and a high-profile state facilitating retention of the catheter in its operative position. A woven mesh forms at least a portion of one of the tube and the retention member. The woven mesh can be formed of filaments heat-settable so that the catheter automatically moves to the high-profile state. Insertion of the catheter can be facilitated using a stylet which can be removed after insertion to permit the catheter to automatically return to its high-profile state.

9 Claims, 7 Drawing Sheets

U.S. PATENT DOCUMENTS

| | | |
|---|---|---|
| 4,747,823 A | 5/1988 | Buchanan |
| 4,893,623 A | 1/1990 | Rosenbluth |
| 4,921,484 A | 5/1990 | Hillstead |
| 5,041,093 A | 8/1991 | Chu |
| 5,147,399 A | 9/1992 | Dellon et al. |
| 5,246,445 A | 9/1993 | Yachia et al. |
| 5,454,790 A | 10/1995 | Dubrul |
| 5,676,688 A | 10/1997 | Jaker et al. |
| 5,882,340 A | 3/1999 | Yoon |
| 5,957,900 A | 9/1999 | Quchi |
| 5,964,806 A | 10/1999 | Cook et al. |
| 6,042,769 A | 3/2000 | Gannon et al. |
| 6,183,492 B1 * | 2/2001 | Hart et al. .................. 606/194 |
| 6,210,370 B1 | 4/2001 | Chi-Sing et al. |
| 6,264,630 B1 * | 7/2001 | Mickley et al. .......... 604/96.01 |
| 6,344,595 B1 | 2/2002 | Phillips et al. |
| 6,558,350 B1 | 5/2003 | Hart et al. |

\* cited by examiner

DRAINAGE CATHETER HAVING AN EXPANDABLE RETENTION MEMBER

BACKGROUND OF THE INVENTION

1. Field of the Invention

This invention generally relates to medical devices and, more specifically, to drainage catheters adapted for use in draining a fluid from a body cavity.

2. Discussion of the Prior Art

Urinary drainage catheters are used to provide an outlet for the urinary bladder when the urethra is compromised or obstructed, such as when the patient is incapable of controlling the urinary system due to sedation or lack of mental capacity. A typical urinary catheter is the Foley catheter, which is a thick-walled rubber tube with an inflatable balloon near its distal end. The Foley catheter is inserted through the urethra and into the bladder cavity. When disposed, the balloon is inflated within the bladder cavity to a size that prevents the distal end from passing back through the bladder neck.

There are several disadvantages associated with the Foley catheter, the most significant of which is patient discomfort due to the construction of the catheter. The typical diameter of a Foley catheter is one-quarter inch or more. This size of catheter is difficult to insert and is very uncomfortable for the patient. Patient frustration sometimes leads to inadvisable patient removal of the catheter, even with the balloon inflated. This of course can be very damaging and traumatic to the patient. The hard rubber tip of the Foley catheter also contributes to patient discomfort. In particular, as the bladder empties, it collapses and the hard rubber tip begins to rub against the wall of the bladder causing irritation.

Thus, there is a need in the art for a drainage catheter that improves patient comfort during insertion and withdrawal of the catheter.

SUMMARY OF THE INVENTION

A drainage catheter having an elongate tube and a retention member disposed at the distal end of the elongate tube. The retention member is adapted for movement between a low-profile state facilitating insertion of the catheter and a high-profile state facilitating retention of the catheter in a body cavity. The retention member is oval or bulb shaped in the high-profile state and is cylindrical in the low-profile state. This construction of the catheter provides for less traumatic insertion and withdrawal of the catheter. A pusher or stylet is provided to facilitate insertion of the catheter. The retention member is preferably formed of a woven mesh that facilitates drainage of fluid into the elongate tube.

These and other features and advantages of the invention will be more apparent with a description of preferred embodiments and reference to the following drawings.

DESCRIPTION OF PREFERRED EMBODIMENTS AND BEST MODE OF THE INVENTION

Co-pending U.S. patent application Ser. No. 09/598,014 filed Jun. 20, 2000, entitled Drainage Catheter, is incorporated herein by reference.

Figure 1:
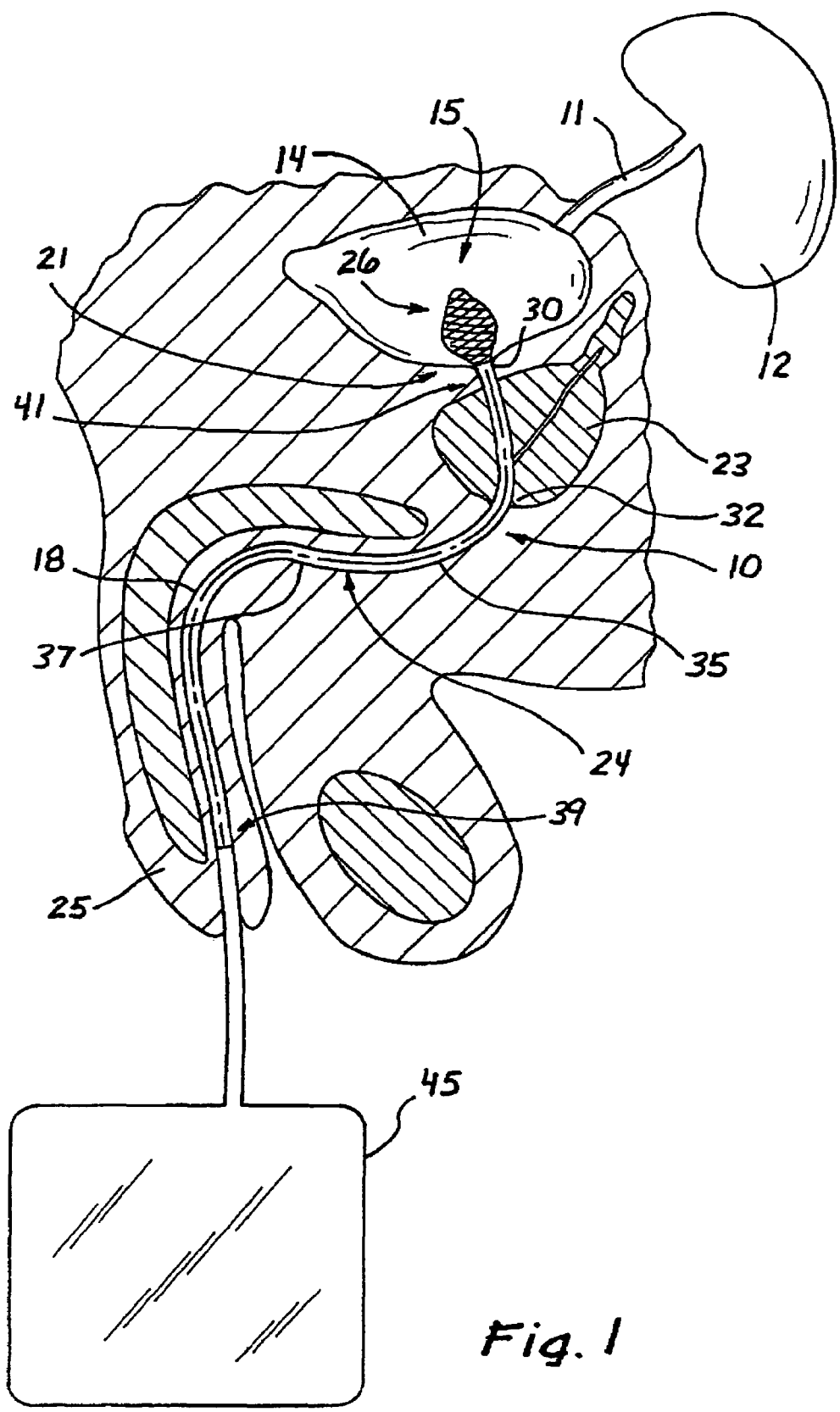
FIG. 1 is a side view of a drainage catheter adapted for use in the urinary tract of a patient.

Referring to FIG. 1, a drainage catheter 10 adapted for use in the urinary tract of a patient is illustrated. The urinary tract includes a ureter 11 extending in fluid communication between a kidney 12 and a bladder 14 having a bladder cavity 15. A urethra 18 begins at a bladder neck 21 and passes outwardly through a prostate 23 and a meatus 25 of a penis 27. When urethra 18 is compromised or obstructed, urine cannot naturally drain from bladder 14 and it becomes desirable to open urethra 18 or otherwise provide a fluid passage from bladder 14 through urethra 18 and meatus 25.

Catheter 10 includes an elongate tube 24 having a wall 35 extending distally to a retention member 26. Tube 24 extends along an axis 37 between a proximal end 39 and a distal end 41. Retention member 26 can be formed of a mesh. With catheter 10 operatively positioned, urethra 18 is opened or otherwise augmented with a passage through tube 24 to drain urine from bladder 14. A drainage conduit 45 can be connected at the proximal end of tube 24 to gather urine in a collection bag 51.

Figure 2A:
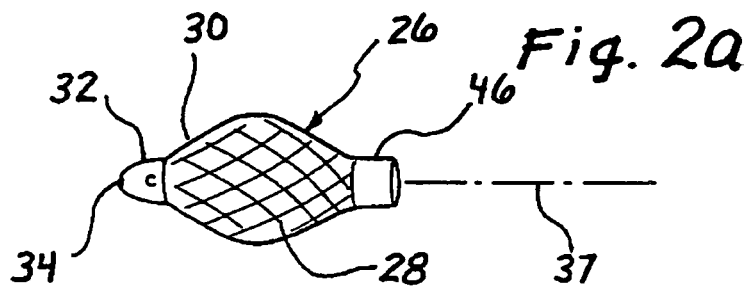
FIGS. 2a-2f illustrate different configurations of a drainage catheter in accordance with an embodiment of the invention.
Figure 2B:
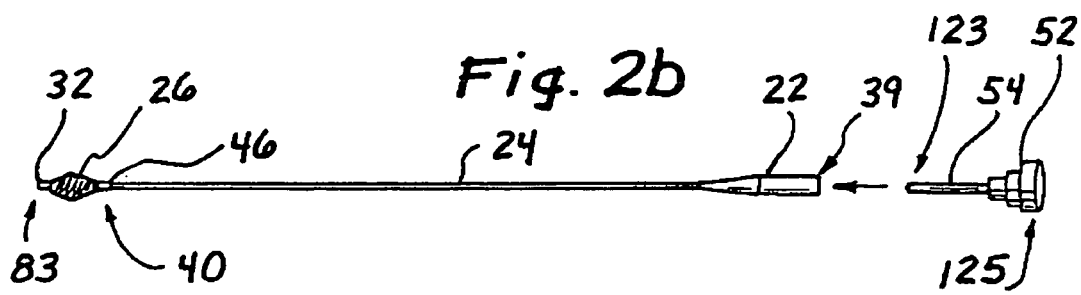
Figure 2C:
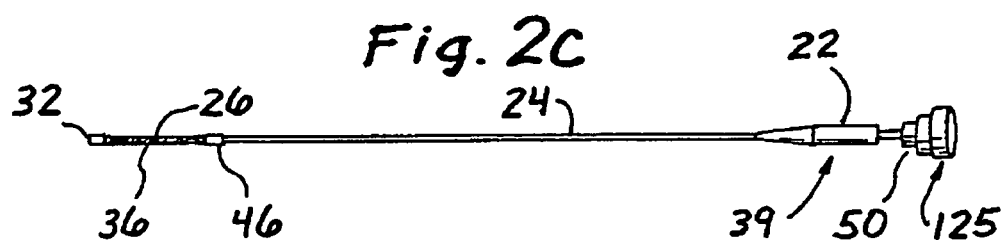
Figure 2D:
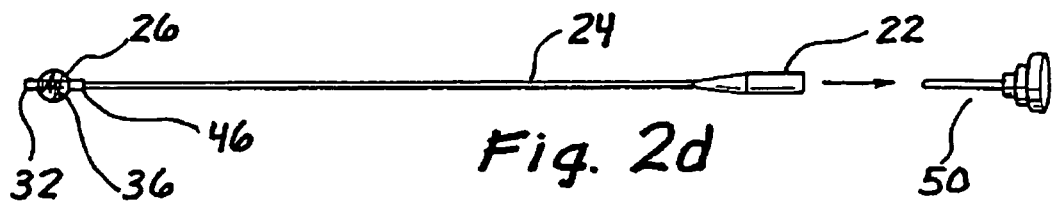

FIGS. 2a-2f illustrate different configurations of catheter 10 in greater detail. Catheter 10 further comprises a hub 22 at the proximal end of tube 24, a stop ledge 36 near a distal end of tube 24 and at least one hole 38 drilled along the distal end of tube 24 for draining fluid from bladder 14. Retention member 26 can be formed from filaments forming a mesh 28 as illustrated in FIG. 2a. Retention member 26 further includes a tethered bushing 32 and a sliding bushing 46. A through lumen 34 can be provided at an end of tethered bushing 32, preferably along axis 37. To reduce the profile of retention member 26, the preferred longitudinal cross-section of retention member 26 is cylindrical when collapsed and resembles a bulb when fully deployed as illustrated in FIGS. 2c and 2d, respectively.

In particular, during placement of retention member 26 as illustrated in FIG. 2c, sliding bushing 46 moves toward the proximal end of tube 24 causing retention member 26 to compress into a cylindrical configuration in a low-profile state. After placement of retention member 26 in urethra 18, sliding bushing 46 moves toward stop ledge 36 as illustrated in FIG. 2d so as to expand retention member 26 to its oval or bulb shape for bladder retention in a high-profile state. In other words, the oval or bulb shape profile of retention member 26 will engage with the bladder wall when the catheter is retracted.

In a preferred construction of retention member 26, filaments forming mesh 28 are woven and movable relative to each other. This characteristic enables retention member 26 to be stretched between the low-profile state and the high-profile state. When the filaments are made of polyester or some other heat-settable material, mesh 28 can be heat set in the high-profile state such that retention member 26 is biased to the high-profile configuration. When mesh 28 is stretched during placement of retention member 26, the filaments elongate providing retention member 26 with the low-profile configuration. That is, the filaments move to a more parallel relationship with axis 37 as retention member 26 is drawn to the low-profile state having a significantly reduced cross-section.

Figure 3A:
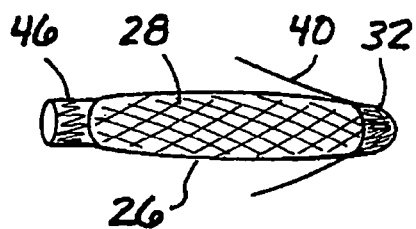
FIGS. 3a-3d illustrate different embodiments of the invention for maintaining the position of a retention member in the bladder.
Figure 3B:
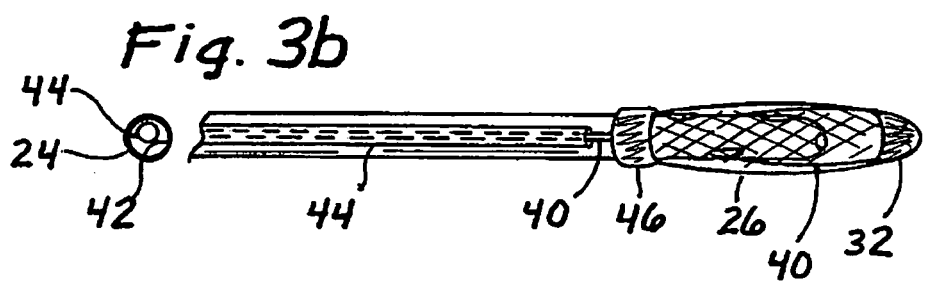
Figure 3C:
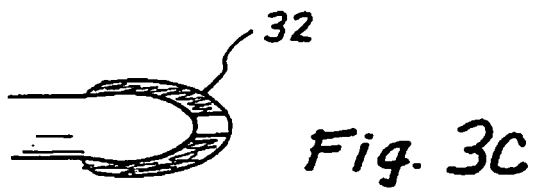
Figure 3D:
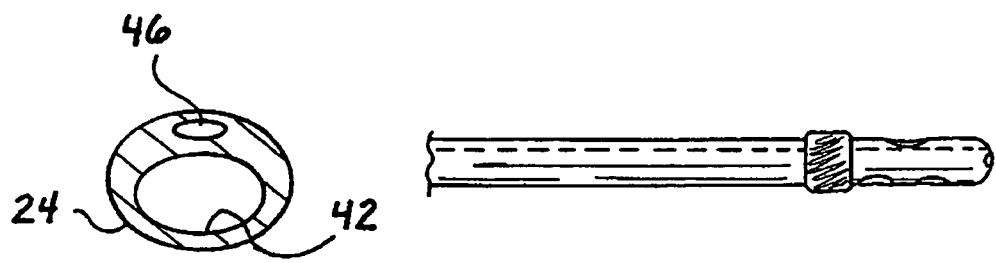

Another feature of the invention is it maintains the position of retention member 26 in bladder 14 even when tube 24 is bent and/or coiled. Referring to FIGS. 3a-3d, at least one suture 40 is operatively attached to tethered bushing 32 at the tip of the catheter to reduce movement of retention member 26 and to secure retention member 26 to the catheter tip even when tube 24 is bent and/or coiled. In particular, retention member 26 is secured to catheter 10 by securing one end of suture 40 to tethered bushing 32, running suture 40 along an inner diameter (I.D.) 42 of tube 24, and securing the other end of suture 40 near the proximal end of tube 24 as further discussed below. In another embodiment of the invention, a separate tube 44 confining suture 40 (see FIG. 3b) is provided within the I.D. 42 of tube 24. In yet another embodiment of the invention, suture 40 is confined within a lumen 46 that is incorporated into tube 24 as illustrated in FIG. 3d.

Another feature of the invention is it provides a soft tip catheter allowing for less traumatic interface between the catheter and the ureteral cavity. In particular, tethered bushing 32 has a soft tip that provides for less traumatic interface between catheter 10 and urethra 18. In a preferred embodiment of the invention, soft tip tethered bushing 32 is molded onto a braided structure or mesh 28 of retention member 26. Alternatively, soft tip tethered bushing 32 can be molded and then attached to retention member 26 by adhesive or with a snap-fit mechanism. An advantage of soft tip tethered bushing 32 is it can resist puncturing and damaging of the ureteral wall during insertion. In particular, soft tip tethered bushing 32 can deflect during placement of catheter 10 and enables it to follow the path of least resistance rather than puncturing through an obstruction. Soft tip tethered bushing 32 can be made from CFlex, Kraton, silicone dispersion, Tecoflex, chronothane Flex or any foreseeable soft material that can be used inside a body cavity.

Figure 4A:
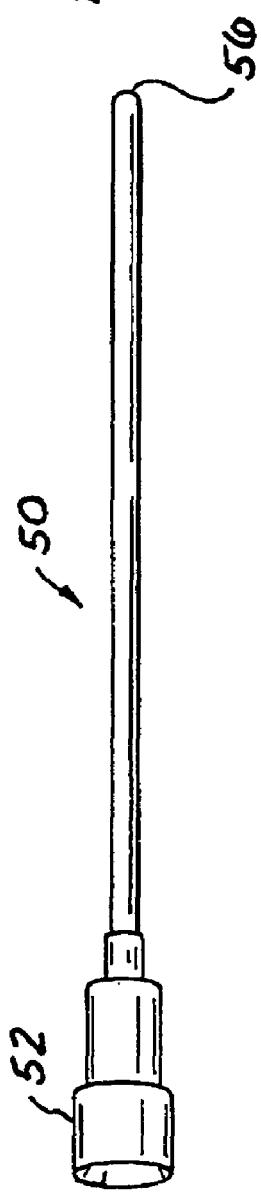
FIGS. 4a-4c illustrate different embodiments of a pusher or stylet of the invention.
Figure 4B:
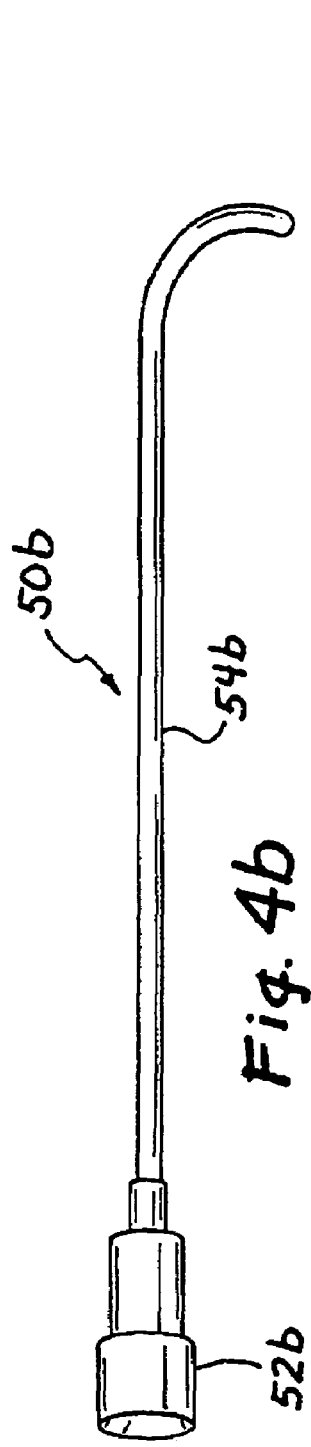
Figure 4C:
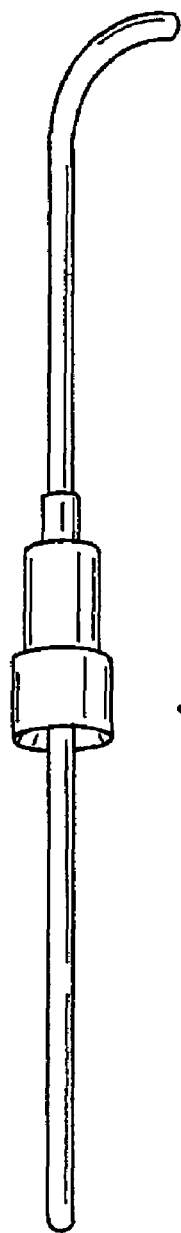

FIGS. 4a-4c illustrate different embodiments of pusher or stylet 50 of the invention for providing ease of insertion and placement of a catheter in a bladder. To provide for ease of insertion and placement of catheter 10, tube 24 and retention member 26 need appropriate stiffness. However, patient comfort commands a soft and flexible construction of the catheter body and retention member. The present invention achieves these opposing requirements by providing a pusher or stylet 50 having proper column strength to facilitate insertion of a catheter having a soft and flexible body and retention member. Stylet 50 comprises a handle 52 and a body 54 having a tip 56. Handle 52 is inserted in catheter hub 22 so as to run along the center of tube 24 up to the catheter distal tip. Stylet 50 is preferably straight in order to keep retention member 26 inline with tube 24. Stylet 50 can be made from a plastic tube, a solid rod or a malleable material incorporated within a plastic body. Alternatively, a malleable stylet can be used without the plastic casement.

FIG. 4b illustrates a curved stylet 50b having a handle 52b and a curved body 54b. Depending on the needs of a procedure and/or a patient's anatomy, a physician can choose between a straight stylet and a curved stylet. Curved stylet 50b can be used to position retention member 26 through more tortuous paths. It is preferable that the stylet handle is operatively removable from the stylet body such that it can be used with either a straight body or a curved body stylet. Similarly, hub member 22 can be free to move along tube 24. Hub 22 can have an internal configuration that mates to an additional feature attached to tube 24. These features mate as a one-way snap-fit assembly. Curved stylet 50b can be made from a malleable material that allows a user to shape the stylet in any desired shape, or can be made from a malleable material incorporated within plastic.

Figure 2E:
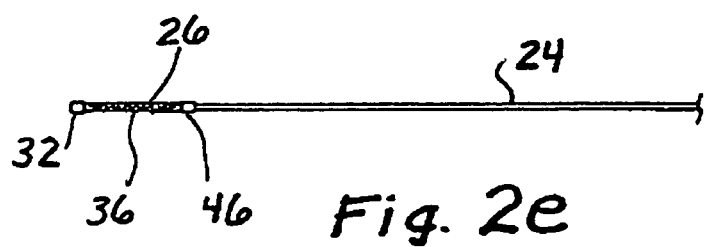
Figure 2F:
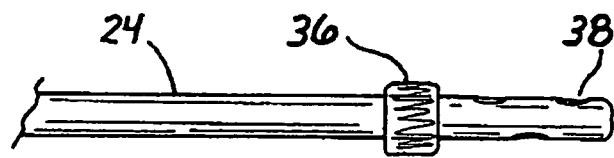

Referring back to FIGS. 2b-2d, a preferred method for moving catheter 10 to an operative position within urethra 18 and bladder 14 is illustrated. In FIG. 2b, catheter 10 is illustrated in its normal state with its proximal end 39 and distal end 40 extending along axis 37. In an initial step of insertion, stylet 50 is provided with a distal end 123 and a proximal end 125. Distal end 123 of stylet 50 can then be inserted into proximal end 39 of catheter 10 and moved distally along tube 24 into retention member 26 where it contacts distal tip 83 of catheter 10. This contact fixes distal end 123 of stylet 50 at distal tip 83 of catheter 10. Grasping proximal end 125 of stylet 50 in one hand and proximal end 39 of catheter 10 in the other hand, these two ends can be moved toward each other as illustrated in FIG. 2c. As proximal end 125 advances toward proximal end 39, retention member 26 is drawn down onto stylet 50. As a result, the enlarged size of retention member 26 is drawn down to substantially the same diameter as tube 24. Once catheter 10 is operatively positioned with its distal tip 83 in bladder 14, stylet 50 can be removed thereby permitting retention member 26 to expand automatically to its high-profile state as illustrated in FIG. 2d. This natural axial contraction and radial expansion of catheter 10 will automatically move retention member 26 to its enlarged state. Once catheter 10 is no longer needed for draining bladder 14, it can be removed with minimal patient discomfort by cutting tube 24 near its proximal end to collapse retention member 26 as illustrated in FIG. 2e. By cutting tube 24, the suture 40 placed inside tube 24 for securing retention member 26 is also cut and, as a result, retention member 26 collapses. The collapsed position of retention member 26 ensures the lowest profile and easy removal of catheter 10.

Figure 5A:
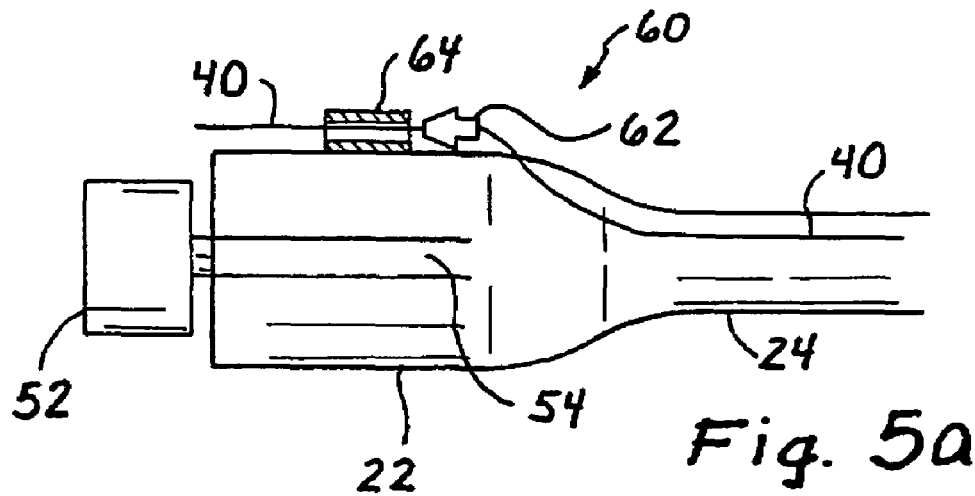
FIGS. 5a-5c illustrate different embodiments of a snap-fit mechanism for deploying the retention member.
Figure 5B:
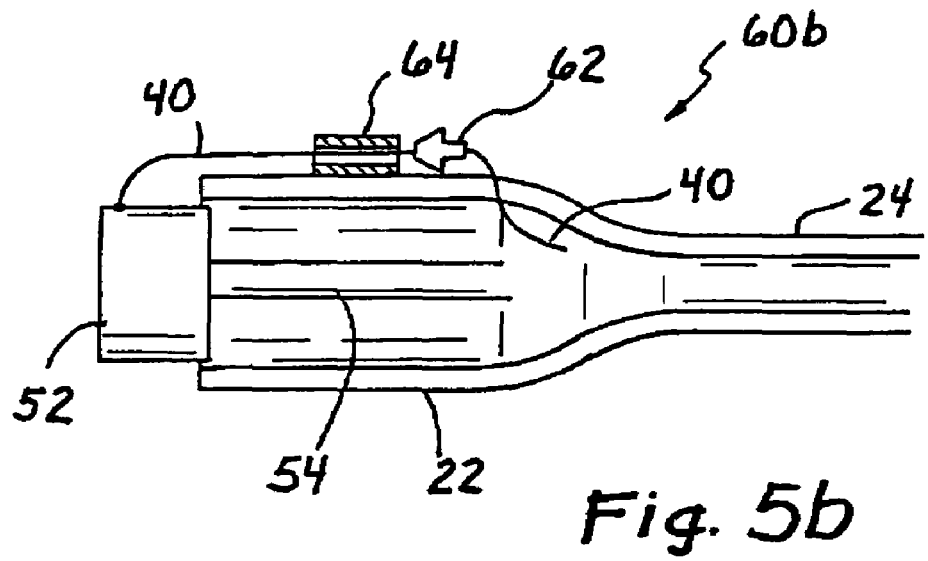
Figure 5C:
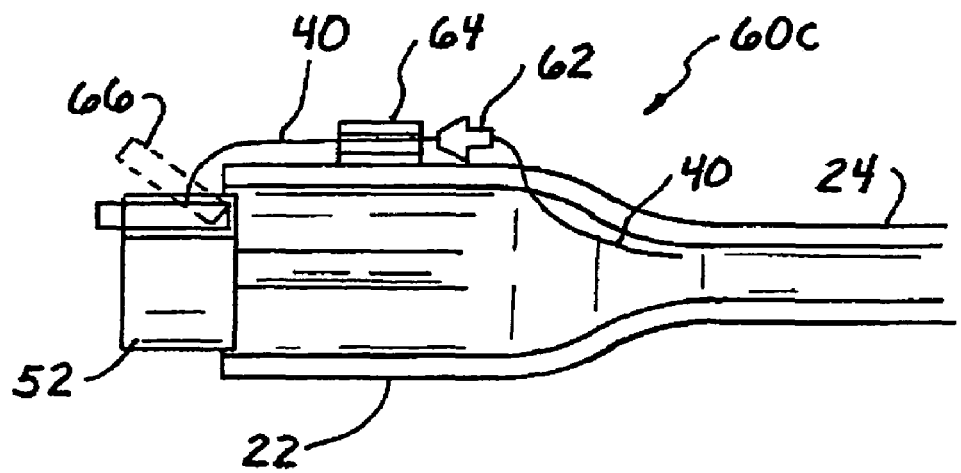

FIGS. 5a-5c illustrate different embodiments of a one-way snap-fit mechanism that allows a user to activate or deploy retention member 26 from outside a patient's body after placement of retention member 26 in bladder 14. Snap-fit mechanism 60 comprises a one-way plug 62 having suture 40 incorporated therethrough and a collar 64. Suture 40 is placed within inner diameter 42 of tube 24 such that it can be pulled through catheter hub 22. Suture 40 can be used to pull plug 62 through collar 64 so as to secure and deploy retention member 26 to the high-profile state having an oval or bulb shape. In one embodiment of the invention, suture 40 can be pulled until plug 62 is secured to collar 64 on hub 22 as illustrated in FIG. 5a. In another embodiment of the invention, an end of suture 40 can be attached to stylet handle 52 such that stylet 50 can be pulled to deploy retention member 26 to its bulb shape in the high-profile state as illustrated in FIG. 5b. Once retention member 26 has been deployed and suture 40 has been pulled to a proper distance, suture 40 can breakaway allowing for removal of stylet 50. In yet another embodiment of the invention as illustrated in FIG. 5c, the suture end can be attached to a mechanism 66 that snaps into stylet handle 52. Once retention member 26 has been deployed and suture 40 has been pulled to a proper distance, the user can release suture 40 by pulling the mechanism 66 out of stylet handle 52.

Figure 6:
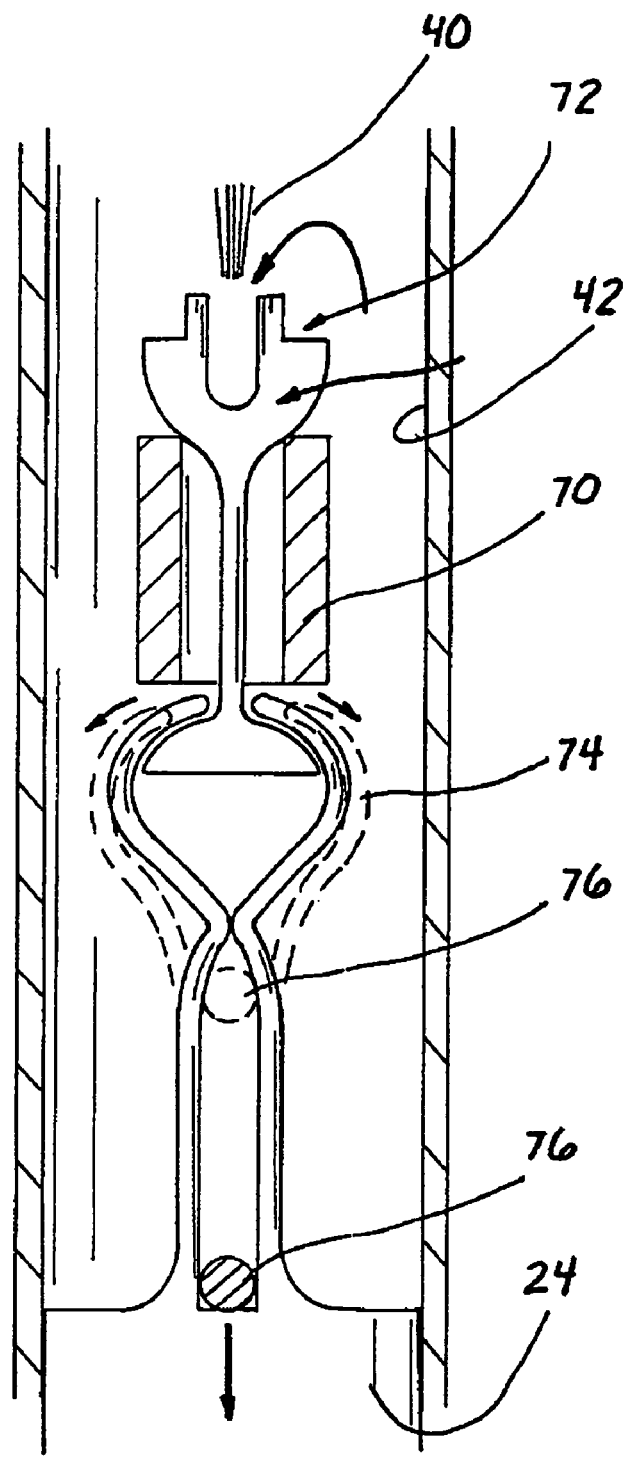
FIG. 6 illustrates a mechanism for deploying the retention member and releasing the suture assembly in a single motion in accordance with an embodiment of the invention.

FIG. 6 illustrates a mechanism for deploying retention member 26 and releasing a suture assembly in a single motion such as removal of the stylet handle. In one embodiment, the mechanism comprises a housing or collar 70 attached within tube 24 or on hub 22 for retaining a ratcheting member 72. Ratcheting member 72 operates to hold suture 40 and has a built in collapsible back end for snap action when pulled through collar 70. Ratcheting member 72 slides axially along tube 24 pulling on suture 40 until retention member 26 is deployed. Stylet handle 125 comprises a pin 76 and a pair of extensions or snap claws 74 operatively attached to an end of ratcheting member 72. As stylet handle 125 is being removed from catheter 10, ratcheting member 72 is being pulled through collar 70 by snap claws 74 to deploy retention member 26. In the same motion of removing stylet handle 125 from catheter 10, snap claws 74 will come into contact with pin 76, which causes snap claws 74 to cam to an open position thereby releasing ratcheting member 72. An advantage of the mechanism of the invention is it is utilized as a one-handed push pull mechanism to activate retention member 26. In another embodiment of the invention, a rotating mechanism can be incorporated to activate retention member 26. This rotating mechanism comprises a housing that retains a ratcheting member. The ratcheting member winds the suture onto itself until retention member 26 is deployed.

FIGS. 7a-7d illustrate different embodiments of a mechanism to collapse retention member 26 for easy catheter removal. A feature of the invention is to preload catheter retention member 26 and assist it to a collapsed position after the securing suture 40 is cut. In other words, when the securing suture 40 is cut, retention member 26 immediately advances to a collapsed position. An advantage of the collapsed position is it ensures the lowest profile of retention member 26 and easy removal of catheter 10. The invention provides a member 80 that can store potential energy for assisting retention member 26 to a collapsed position once the securing suture 40 is cut at the distal end of tube 24. Member 80 can be made from a metallic or nonmetallic material. Some specialty material such as memory wire and plastics may also be incorporated to assist retention member 26.

Figure 7A:
FIGS. 7a-7d illustrate different embodiments of a mechanism of the invention for providing fast collapse of the retention member for easy catheter removal.
Figure 7B:
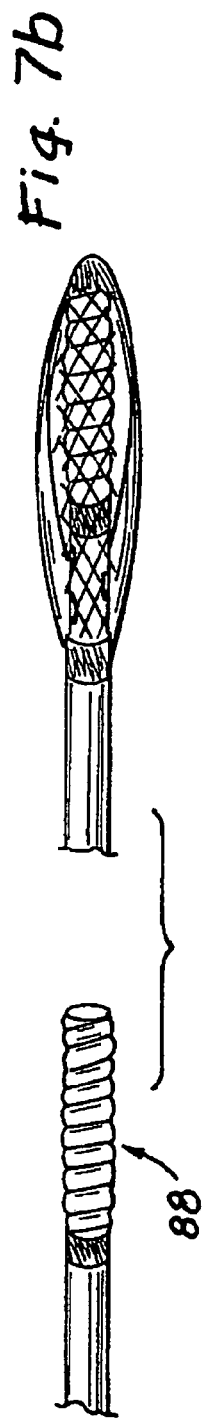
Figure 7C:
Figure 7D:
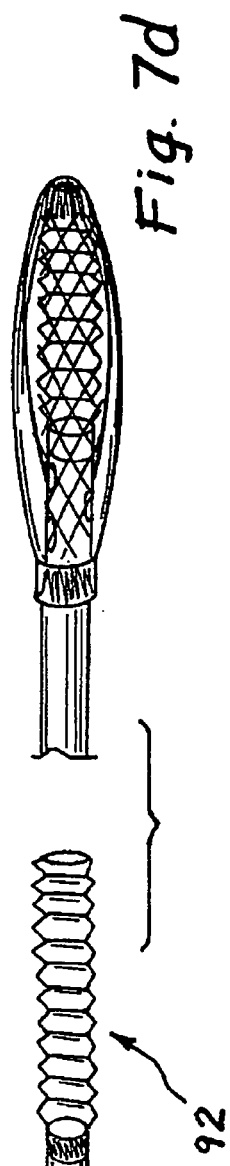

FIG. 7a illustrates one embodiment of member 80 which comprises one or more wires 82 connected from the distal end of tube 24 to tethered bushing 32 of retention member 26. When retention member 26 is deployed to an oval or bulb shape, wire 82 will bend within the inner diameter 86 of retention member 26. Bending of wire 82 will store potential energy into the wire member. This potential energy can then be used to assist retention member 26 to collapse to its low-profile shape once suture 40 is cut. In another embodiment of the invention as illustrated in FIG. 7b, a spiral shaped wire such as a spring 88 with a varying number of coils can effectively store and release enough force to collapse retention member 26 to its low-profile shape once suture 40 is cut. In yet another embodiment of the invention as illustrated in FIG. 7c, a combination of spring and wire such as a coil wire 90 maybe used to further take advantage of the potential energy when deploying retention member 26. Another device having the ability to store potential energy is a bellows 92 as illustrated in FIG. 7d. Bellows 92 is made from a series of convoluted shapes that collapse or contract when retention member 26 is deployed and release the stored potential energy once suture 40 is cut.

Although the disclosed retention member of the invention has a collapsible oval or bulb shape that facilitates both insertion and withdrawal of the drainage catheter, it will be apparent that other retention members having different collapsible shapes also facilitate insertion and withdrawal of the drainage catheter.

With the wide variety of features and advantages associated with both the apparatus and method of the present invention, one is cautioned not to restrict the concept merely to the embodiments disclosed, but rather to determine the scope of the invention only with reference to the claims.

The invention claimed is:

1. A drainage catheter adapted to drain fluid from a body cavity through a body conduit, comprising:
    an elongate tube having a proximal end and a distal end, and being sized and configured for insertion into the body cavity;
    an expandable retention member disposed at the distal end of the elongate tube and being adapted for movement between a low-profile state facilitating insertion of the catheter into the body cavity, and an expanded high-profile state facilitating retention of the distal end of the catheter in the body cavity;
    a stylet removably insertable into the elongate tube to facilitate insertion and placement of the catheter in the body cavity; and
    a ratcheting member having a suture attached thereto and a collapsible backend for snap-action when pulled through a collar disposed within the elongate tube, said ratcheting member slides along the elongate tube pulling on said suture until said retention member is deployed.

2. The drainage catheter of claim 1, wherein the retention member is formed from a plurality of woven filaments, the woven filaments being permeable by the fluid to facilitate drainage of the fluid from the body cavity.

3. The drainage catheter of claim 2, wherein the woven filaments form a mesh.

4. The drainage catheter of claim 1, wherein said stylet further comprises an elongate body and a handle disposed along the elongate body.

5. The drainage catheter of claim 4, wherein said elongate tube further comprises a hub sized and configured to receive said handle of said inserting stylet.

6. The drainage catheter of claim 1, wherein said stylet is formed from one of a plastic tube, a solid rod or a malleable material incorporated within plastic.

7. The drainage catheter of claim 4, wherein said handle is removably connected to said elongate body.

8. The drainage catheter of claim 7, wherein said elongate body is one of a straight or a curved body stylet.

9. The drainage catheter of claim 1, wherein said stylet further comprises a plurality of extensions for operatively attaching an end of the ratcheting member to pull said ratcheting member through the collar to deploy said retention member.

\* \* \* \* \*